United States Patent
Matesevac et al.

(10) Patent No.: US 6,267,970 B1
(45) Date of Patent: Jul. 31, 2001

(54) CREAM COSMETIC BASE WITH POWDERY FEEL

(75) Inventors: Ronald A. Matesevac, Teaneck; Beatriz N. Bennett, Ramsey, both of NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 09/046,321

(22) Filed: Mar. 23, 1998

(51) Int. Cl.[7] .......................... A61K 7/021; A61K 7/035; A61K 6/00; A61K 9/14

(52) U.S. Cl. .................. 424/401; 424/63; 424/69; 424/489; 514/844

(58) Field of Search ................. 424/401, 78.03, 424/63, 69, 489; 514/844

(56) References Cited

U.S. PATENT DOCUMENTS

| | | | |
|---|---|---|---|
| 3,947,571 | * | 3/1976 | Murphy et al. ............ 424/64 |
| 3,947,574 | * | 3/1976 | Murphy et al. ............ 424/64 |
| 4,511,496 | | 4/1985 | Matsumoto et al. . |
| 4,536,315 | | 8/1985 | Ramachandran . |
| 4,563,346 | * | 1/1986 | Deckner ................... 424/59 |
| 4,568,539 | | 2/1986 | Ashton et al. . |
| 4,707,354 | | 11/1987 | Garlen et al. . |
| 4,778,783 | | 10/1988 | Gondra . |
| 4,820,510 | * | 4/1989 | Arraudeau et al. ......... 424/63 |
| 4,822,603 | * | 4/1989 | Farris et al. ............. 424/66 |
| 4,913,896 | | 4/1990 | Harvey . |
| 4,917,891 | | 4/1990 | Kaufman et al. . |
| 4,940,584 | | 7/1990 | Tararuji et al. . |
| 4,983,388 | | 1/1991 | Kuwata et al. . |
| 5,000,947 | | 3/1991 | Nichols . |
| 5,011,690 | | 4/1991 | Garvey et al. . |
| 5,043,161 | | 8/1991 | Scarpelli et al. . |
| 5,069,897 | | 12/1991 | Orr . |
| 5,108,737 | | 4/1992 | Dunphy et al. . |
| 5,176,903 | | 1/1993 | Goldberg et al. . |
| 5,223,251 | | 6/1993 | Nichols . |
| 5,234,682 | | 8/1993 | Macchio et al. . |
| 5,271,934 | | 12/1993 | Goldberg et al. . |
| 5,292,530 | | 3/1994 | McCrea et al. . |
| 5,310,547 | | 5/1994 | Dunphy et al. . |
| 5,338,535 | | 8/1994 | Berndt . |
| 5,356,626 | | 10/1994 | Da Cunha et al. . |
| 5,356,627 | * | 10/1994 | Da Cunha et al. .......... 424/401 |
| 5,378,468 | | 1/1995 | Suffis et al. . |
| 5,391,374 | * | 2/1995 | Charbonneau et al. ...... 424/401 |
| 5,407,678 | | 4/1995 | Rose et al. . |
| 5,449,511 | | 9/1995 | Coe . |
| 5,453,281 | | 9/1995 | Whistler . |
| 5,482,714 | * | 1/1996 | Jones et al. .............. 424/401 |
| 5,490,982 | | 2/1996 | Siciliano . |
| 5,496,861 | | 3/1996 | Rouse, 3 et al. . |
| 5,505,937 | * | 4/1996 | Castrogiovanni et al. ... 424/401 |
| 5,508,259 | | 4/1996 | Holzner et al. . |
| 5,525,588 | * | 6/1996 | Michetti ................... 512/4 |
| 5,607,666 | | 3/1997 | Masson et al. . |
| 5,626,155 | | 5/1997 | Saute . |
| 5,626,856 | | 5/1997 | Berndt .................... 424/401 |
| 5,632,996 | | 5/1997 | Ramirez et al. ........... 424/401 |
| 5,662,937 | | 9/1997 | McCuaig . |
| 5,670,159 | | 9/1997 | Morton et al. . |
| 5,674,509 | | 10/1997 | Date et al. . |
| 5,674,511 | | 10/1997 | Kacher et al. . |
| 5,679,361 | | 10/1997 | Pradier et al. . |
| 5,690,945 | | 11/1997 | Bui-Bertrand et al. . |
| 5,833,964 | | 11/1998 | Linn et al. ............... 424/65 |

* cited by examiner

Primary Examiner—Thurman K. Page
Assistant Examiner—S. Tran
(74) Attorney, Agent, or Firm—Ohlandt, Greeley, Ruggiero & Perle, LLP

(57) ABSTRACT

A cream composition is disclosed that includes about 10 to about 30 weight percent of a wax having ozokerite, myristyl myristate, petrolatum, and hydrogenated castor oil; about 30 to about 70 weight percent of a powder having a starch selected from the group consisting of corn starch, oat starch and a combination thereof; and a volatile component having a volatile selected from the group consisting of cyclomethicone, isoeicosane and a combination thereof. The cream composition preferably includes a microencapsulated fragrance.

35 Claims, No Drawings

CREAM COSMETIC BASE WITH POWDERY FEEL

FIELD OF THE INVENTION

The present invention relates generally to a cream base for use in a variety of cosmetic compositions. More particularly, the present invention relates to a cream base that has a powdery finish and feel when applied to the skin. This cream base is preferably used to deliver fragrance, more preferably microencapsulated fragrance, to the skin.

BACKGROUND OF THE INVENTION

Various cosmetic base compositions are known in the art, including powders, lotions, gels, sticks and creams. While the lines of demarcation between these types of base compositions are at times inexact, each type is seen by consumers as having different positive and negative attributes. For example, powders are often viewed as drying and hard to control. Lotions can be perceived as overly wet, requiring time to dry, and can also be perceived as greasy or oily. Creams can be seen as excessively heavy. Thus, a demand exists for products that combine the positive attributes of more than one such cosmetic base, without the perceived limitations. Certain such products have been commercialized, including "dry lotions". However, no product is known that successfully provides a creamy base that has good payoff and leaves a silky, powdery finish when applied to the skin.

SUMMARY OF THE INVENTION

Accordingly, it is an object of the present invention to provide a cosmetic cream base composition that leaves a silky, powdery finish when applied to the skin.

It is another object of the present invention to provide such a cosmetic cream base that has good payoff, namely in releasing a proper amount of product (sufficient but not excessive) to the applicator when light pressure is applied to the cosmetic by the applicator.

It is a further object of the present invention to provide such a cosmetic cream base that is suitable for delivery of microencapsulated fragrance to the skin.

It is still another object of the present invention to provide a cosmetic cream base that is suitable for delivery of other cosmetic ingredients, such as treatment agents and non-microencapsulated fragrances, to the skin.

Accordingly, the present invention is a cream composition that includes about 10 to about 30 weight percent of a wax component having ozokerite, myristyl myristate, petrolatum, and hydrogenated castor oil; about 30 to about 50 weight percent of a powder component having a starch selected from the group consisting of corn starch, oat starch and combinations thereof; and a volatile component having a volatile selected from the group consisting of cyclomethicone, isoeicosane and combinations thereof. The cream composition preferably includes a microencapsulated fragrance.

DESCRIPTION OF THE PREFERRED EMBODIMENTS

The present invention provides a unique cosmetic cream base composition that is suitable for use alone as an emollient cream, or in combination with one or more additional cosmetic ingredients. Such additional cosmetic ingredients include preservatives, treatment agents, humectants and fragrances. Most preferably, the cosmetic cream base composition of the present invention is used in conjunction with microencapsulated fragrance to form a cream fragrancing composition that can be applied directly to the skin of the wearer.

The preferred cosmetic cream base composition of the present invention includes a substantial powder component in combination with a wax component and a volatile component. The powder component preferably includes one or more of the following powders: corn starch, oat starch and spherical silicone dioxide. The use of starch is preferred for its appealing, soft texture and smooth finish, as well as for its ability to absorb or adsorb the waxes and fluids of the composition of the present invention. Modified starches that are powders (not liquids) may also be used. It is preferred that the starch or starches used in the compositions of the present invention be processed so they do not have a whitening effect when rubbed on the skin. The use of spherical silicone dioxide is preferred for its ability to enhance the feel of the starch component on application to the skin.

Starch and other powders are preferably present in the preferred cream base composition at about 30 to about 70 weight percent of the composition. In a fragrancing composition containing microcapsules (discussed below), the starch and other powders more preferably are about 40 to about 55 weight percent and most preferably about 43.5 weight percent of the total weight of the composition. The weight percent of the starch component is preferably adjusted to accommodate the powdery particulate fragrance microcapsules when they are present. Without the microencapsulated fragrance, a higher weight percent of powders is most preferred, namely about 55 weight percent.

The wax component of the cosmetic cream base composition of the present invention preferably includes one or more of the following waxy components: ozokerite, myristyl myristate, petrolatum and hydrogenated castor oil. Other waxes would work in the compositions of the present invention, provided there is at least one microcrystalline wax present for stability. Ozokerite and petrolatum are the preferred microcrystalline waxes for use in the present invention. Ozokerite provides the structure of the preferred product. Petrolatum is used to help prevent syneresis over time (microcrystalline waxes perform this function generally) without making the product too hard or raising the melting point above a temperature that is easy to process. Hydrogenated castor oil adds additional structure and controls the hardness of the product. Myristyl myristate is a solid ester wax at room temperature, and is used to give an aesthetically pleasing feel to the product.

Wax is preferably present in the cosmetic cream base composition of the present invention at about 10 to about 30 weight percent. More preferably, wax is about 15 to about 20 weight percent, and most preferably about 18.5 weight percent of the total weight of the composition.

As discussed above, a preferred cosmetic cream base composition of the present invention includes a volatile component. This volatile component adds to the silky finish of the cosmetic cream base composition when it is applied to the skin. Preferably, this volatile component includes cyclomethicone, isoeicosane, or a combination of the two. More preferably, the cyclomethicone is cyclomethicone pentamer. Other volatile components would function in the compositions of the present invention as long as they are able to be processed at the temperatures needed to melt waxes, e.g. at about 170 to about 180° F., without flashing off. The volatile component is preferably present at about 5 to about 20 weight percent, with about 13 weight percent being more preferred. Most preferably, the volatile component is about 5 weight percent of cyclomethicone pentamer and about 8 weight percent isoeicosane.

A preferred cosmetic cream base composition of the present invention includes a liquid emollient component in combination with the wax component. The liquid emollient component preferably is present at about 5 to about 10 weight percent, and more preferably at about 8 weight percent. The liquid emollient component, preferably including C12–15 alcohols benzoate, is made of a non-greasy emollient or combination of emollients that are nonirritating to the eyes and skin. The emollients preferably impart a dry lubricating feel to skin.

A preferred composition according to the present invention includes a solid emollient in addition to the wax component discussed above. In particular, dialkyl fumarate is a solid emollient imparting an elegant, non-greasy feel that is preferred for use as a solid emollient. Dialkyl fumarate is preferably used for its ability to enhance the feel of the waxy components on application to the skin. It is a waxy emollient that melts at about body temperature. For the purposes of the present invention, dialkyl fumarate, and di-C12–15-alkyl fumarate preferably, can be considered a wax, but it is preferably considered an emollient.

The solid emollient component preferably is present at about 2 to about 10 weight percent, and more preferably at about 5 weight percent. When a liquid emollient is used in combination with a solid emollient, the emollient component is preferably present at a weight percent of up to about 20 weight percent, with about 13 weight percent being more preferred.

Furthermore, the cosmetic cream base composition of the present invention preferably includes a fragrance. More preferably, the fragrance includes a microencapsulated fragrance in combination with a non-microencapsulated fragrance, although either type of fragrance may be added alone to the cosmetic cream base composition of the present invention.

The microencapsulated fragrance gives the composition a renewable fragrance that can be activated by friction against the skin bearing the composition. This friction can be intentionally applied by the wearer to revive the fragrance (by rubbing the skin and rupturing more of the microcapsules) or can occur due to normal movement and friction encountered during normal daily activities. The addition of a non-microencapsulated fragrance to the composition gives the composition a readily detectable scent, to make the product appealing even before it is applied to the skin. Thus, an optimal combination of microencapsulated fragrance and conventional fragrance can be used in the cosmetic cream base composition of the present invention to provide pleasing scent in the package, on application, and long after initial application.

Fragrance is preferably present in the cosmetic cream base composition of the present invention at about 0.01 to about 20 weight percent. More preferably, when the composition is to be used as a cream cologne, fragrance is present at about 5 to about 15 weight percent, with about 12 weight percent being most preferred. Of this fragrance component, it is preferred that about half be microencapsulated fragrance, and about half be non-microencapsulated fragrance, with a more preferred ratio of 5 parts by weight microencapsulated fragrance to 7 parts by weight conventional fragrance. While the preferred microencapsulated fragrances have a powdery consistency, they are not considered powders when determining preferred powder weight percents for purposes of this invention.

Other optional components can be added to the cosmetic cream base composition of the present invention. For example, preservatives, treatment agents (e.g., vitamins or ceramides), humectants (e.g., lactic acid) can be included in the composition to enhance the appearance or the function of the composition.

It is preferred that the cosmetic cream base composition according to the present invention be substantially anhydrous. It is believed that the addition of substantial amounts of water (over about 5 weight percent) to the composition of the present invention would negatively affect the aesthetics, processing and stability of the product. However, even with the addition of up to about 5 weight percent of water, the compositions of the present invention continue to provide a silky powdery finish on the skin.

A preferred composition according to the present invention has the following formulation:

| Ingredient | Weight Percent |
|---|---|
| Ozokerite 170-D | 4.00 |
| Myristyl myristate | 5.50 |
| Petrolatum | 5.00 |
| Hydrogenated castor oil | 4.00 |
| Isoeicosane | 8.00 |
| Silicone dioxide-spherical | 0.50 |
| DI-12–15 alkyl fumarate | 5.00 |
| Oat starch | 9.50 |
| C12–15 alcohols benzoate | 8.00 |
| Cyclomethicone-pentamer | 5.00 |
| Corn starch-powder 3401 | 33.50 |
| Fragrance | 7.00 |
| Microencapsulated fragrance | 5.00 |

This fragrancing cream sets up well in a jar or a metal pan. It has a slightly iridescent, creamy appearance, and demonstrates good payoff when rubbed with a finger or applicator. It leaves an invisible, smooth, silky, powder-like finish when applied to the skin. Furthermore, it imparts an even fragrance to the skin that can be renewed by rubbing the coated skin.

It is believed that the following ranges of ingredients can be used to produce preferred compositions within the scope of the present invention:

| Ingredient | Weight Percent Range |
|---|---|
| Ozokerite 170-D | 2 to 6 |
| Myristyl myristate | 2 to 7 |
| Petrolatum | 2 to 6 |
| Hydrogenated castor oil | 1 to 7 |
| Isoeicosane | 2 to 12 |
| Silicone dioxide-spherical | 0 to 2 |
| DI-12–15 alkyl fumarate | 0 to 10 |
| Oat starch | 4 to 25 |
| C12–15 alcohols benzoate | 2 to 15 |
| Cyclomethicone | 2 to 10 |
| Corn starch-powder 3401 | 15 to 50 |
| Fragrance | 1 to 12 |
| Microencapsulated fragrance | 0 to 10 |

In addition, the following ingredients can be added to, or substituted for, the foregoing to form other preferred compositions according to the present invention:

| | |
|---|---|
| Aluminum starch octenylsuccinate | 0 to 10 |
| Isohexadecane | 0 to 12 |
| Silicone Fluid SF-96-5 | 0 to 10 |

In regard to preferred methods of processing the compositions of the present invention, if a microencapsulated fragrance is used that contains more than about 10% moisture by weight, it should be pre-mixed with about 10 parts of either or both starches (at a minimum) to one part of microencapsulated fragrance to prevent aggregation or clumping.

The cosmetic cream base composition of the present invention provides a unique consistency and finish, both before and after application to the skin. It is provided to the consumer as a creamy solid or semi-solid that is optimally suited for packaging in a jar or other rigid container. The user finds that the payoff—the ease of removing a small amount of the product for a single application—is excellent. On one hand, excessive force is not necessary to obtain the desired amount. On the other hand, the cream is not so soft that even a minimal application of force separates an excessive amount of product from the packaged cream.

Even more importantly, the cosmetic cream base composition of the present invention leaves a unique silky, powdery finish on the skin as, and after, it is applied by the user. On contact with the skin, the creamy base does not leave a conventional oily, wet or greasy cream residue on the skin, and does not require time to dry. Instead, the cosmetic cream base composition of the present invention, when applied to the skin, provides a powdery finish on the skin. However, this silky powder finish does not leave a powder residue on the skin like conventional powder compositions. In addition, it is not drying to the skin like conventional powder compositions. Moreover, because it is delivered as a cream base, it is not subject to spillage, blowing and other types of inadvertent dispersion, unlike conventional powder compositions.

Various other modifications may be made as will be apparent to those skilled in the art. Thus, it will be obvious to one of ordinary skill in the art that the foregoing description and drawings are merely illustrative of certain preferred embodiments of the present invention, and that various obvious modifications can be made to these embodiments in accordance with the spirit and scope of the appended claims.

What is claimed is:

1. A cosmetic composition comprising:
   a substantially anhydrous cream base having:
      a wax selected from the group consisting of ozokerite, myristyl myristate, petrolatum, hydrogenated castor oil and one or more combinations thereof, wherein said wax is present in an amount about 10 to about 30 percent by weight of said cream base, and said wax includes at least one microcrystalline wax;
      a powder component including corn starch, oat starch or a combination thereof, wherein said powder component is present in an amount about 30 to about 70 percent by weight of said cream base; and
      a volatile component that can be processed at a temperature high enough to process said wax, said volatile component including a volatile substance selected from the group consisting of isoeicosane, cyclomethicone and a combination thereof and said volatile component present in an amount about 5 to about 20 percent by weight of said cream base,
   wherein said cream base has a substantially creamy feel upon an initial application to skin and subsequently develops a substantially powdery feel.

2. The composition of claim 1, further comprising an emollient.

3. The composition of claim 2, wherein said emollient is selected from the group consisting of C12–15 alcohols benzoate, dialkyl fumarate and combinations thereof.

4. The composition of claim 2, wherein said emollient is present at about 5 to about 20 percent by weight of said cream base.

5. The composition of claim 1, wherein said cyclomethicone is cyclomethicone pentamer.

6. The composition of claim 1, further comprising a fragrance.

7. The composition of claim 6, wherein said fragrance is selected from the group consisting of microencapsulated fragrance, nonencapsulated fragrance and a combination thereof.

8. The composition of claim 7, wherein said fragrance is present at about 0.01 to about 20 percent by weight of said cream base.

9. The composition of claim 6, wherein said fragrance is present at about 5 to about 15 percent by weight of said cream base.

10. The composition of claim 7, wherein said fragrance is the combination.

11. The composition of claim 1, wherein said composition is substantially anhydrous.

12. The composition of claim 1, wherein said powder component further includes a spherical silicone dioxide.

13. The composition of claim 1, wherein said powder component is present at about 40 to about 55 percent by weight of said cream base.

14. The composition of claim 1, wherein said wax is present at about 15 to about 20 percent by weight of said cream base.

15. A cosmetic composition comprising:
   a substantially anhydrous cream base consisting essentially of:
      about 10 to about 30 percent by weight of said cream base of a wax selected from the group consisting of ozokerite, myristyl myristate, petrolatum, hydrogenated castor oil, and one or more combinations thereof;
      about 30 to about 70 percent by weight of said cream base of a powder component having a starch selected from the group consisting of corn starch, oat starch and a combination thereof; and
      about 5 to about 20 percent by weight of said cream base of a volatile component that includes a volatile substance selected from the group consisting of cyclomethicone, isoeicosane and a combination thereof,
   wherein said cream base has a substantially creamy feel upon an initial application to skin and subsequently develops a substantially powdery feel.

16. The composition of claim 15, wherein said cyclomethicone is cyclomethicone pentamer.

17. The composition of claim 15, further comprising a fragrance.

18. The composition of claim 17, wherein said fragrance is selected from the group consisting of microencapsulated fragrance, nonencapsulated fragrance and a combination thereof.

19. The composition of claim 17, wherein said fragrance is present at about 0.01 to about 20 percent by weight of said cream base.

20. The composition of claim 17, wherein said fragrance is present at about 5 to about 15 percent by weight of said cream base.

21. The composition of claim 17, wherein said fragrance is the combination.

22. A topical composition comprising:
a substantially anhydrous cream base having:
- a wax selected from the group consisting of ozokerite, myristyl myristate, petrolatum, hydrogenated castor oil and one or more combinations thereof, wherein said wax is present in an amount about 15 to about 20 percent by weight of said cream base;
- a powder component selected from the group consisting of corn starch, oat starch and combinations thereof, wherein said powder component is present in an amount about 40 to about 55 percent by weight of said cream base;
- a volatile component including a volatile substance selected from the group consisting of isoeicosane, cyclomethicone and a combination thereof, said volatile component being present in an amount about 5 to about 20 percent by weight of said cream base; and
- a microencapsulated fragrance present in an amount about 5 to about 15 percent by weight of said cream base, wherein said cream base has a substantially creamy feel upon an initial application to skin and subsequently develops a substantially powdery feel.

23. The composition of claim 22, further comprising an emollient.

24. The composition of claim 23, wherein said emollient is present at about 2 to about 20 percent by weight.

25. The composition of claim 23, wherein said emollient is selected from the group consisting of C12–15 alcohols benzoate, dialkyl fumarate and combinations thereof.

26. The composition of claim 22, wherein said cyclomethicone is cyclomethicone pentamer.

27. The composition of claim 22, further comprising a nonencapsulated fragrance.

28. The composition of claim 22, wherein the composition is substantially anhydrous.

29. The composition of claim 22, wherein said powder component further includes a spherical silicone dioxide.

30. The composition of claim 22, wherein said wax is present at about 15 to about 20 percent by weight of said cream base.

31. The composition of claim 22, wherein said powder present at about 40 to about 55 percent by weight of said cream base.

32. The composition of claim 22, wherein said wax is a microcrystalline wax.

33. The composition of claim 22, wherein said wax is ozokerite, said powder is corn starch and said volatile component is cyclomethicone.

34. The composition of claim 15, further comprising an emollient.

35. The compostion of claim 34, wherein the emollient is selected from the group consisting of $C_{12-15}$ alcohols benzoate, dialkyl fumarate, and a combination thereof.

* * * * *